US00PP21150P3

(12) United States Plant Patent
Egger

(10) Patent No.: US PP21,150 P3
(45) Date of Patent: Jul. 6, 2010

(54) *HEUCHERELLA* PLANT NAMED 'TAPESTRY'

(50) Latin Name: ×*Heucherella*
Varietal Denomination: Tapestry

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 128 days.

(21) Appl. No.: 12/231,834

(22) Filed: Sep. 5, 2008

(65) Prior Publication Data

US 2010/0064402 P1 Mar. 11, 2010

(51) Int. Cl.
*A01H 5/00* (2006.01)

(52) U.S. Cl. ..... Plt./441

(58) Field of Classification Search ..... Plt./441
See application file for complete search history.

(56) References Cited

U.S. PATENT DOCUMENTS

PP14,489 P2 * 1/2004 Oliver ..... Plt./441
PP14,825 P2 * 5/2004 Heims ..... Plt./441

OTHER PUBLICATIONS

UPOV ROM GTITM Computer Database, GTI Jouve Retrieval Software 2009/03 Citation for 'Tapestry'.*

* cited by examiner

*Primary Examiner*—Wendy C Haas
(74) *Attorney, Agent, or Firm*—Klarquist Sparkman, LLP

(57) ABSTRACT

A new and distinct *Heucherella* plant substantially as shown and described, characterized by leaves colored blue green in spring and summer changing to green in the fall and winter with a large dark center following the veins, and a silver veil or overlay, palmately lobed leaves, numerous stalks of warm pink flowers, and excellent vigor.

1 Drawing Sheet

Botanical denomination: ×*Heucherella.*
Variety designation: 'Tapestry'.

The present invention relates to a new and distinct cultivar of ×*Heucherella* and given the cultivar name of 'Tapestry'. *Heucherella* is in the family *Saxifragaceae. Heucherella* 'Tapestry' originated from a controlled cross between *Heuchera* 507 (a proprietary unreleased *Heuchera* spp.), as the seed parent, and an unknown *Tiarella* (massed, proprietary, cut leaf types) as the pollen parent. 'Tapestry' was the best selection of a large group of seedlings from the cross. It has very attractive foliage and flowers.

This new *Heucherella* is distinguished by:

1. leaves colored blue-green in spring and summer changing to green in the fall and winter with a large dark center following the veins, and a silver veil or overlay,
2. palmately lobed leaves,
3. numerous stalks of warm pink flowers, and
4. excellent vigor.

This new cultivar has been reproduced only by asexual propagation (cuttings and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The new variety has not been evaluated under all possible environmental conditions. The phenotype may vary with variations in environment without a change in the genotype of the plant.

BRIEF DESCRIPTION OF THE DRAWINGS

FIG. 1 shows a one-year-old *Heucherella* 'Tapestry' growing in the ground in the trial bed in Canby, Oreg. in mid-spring.

FIG. 2 shows a one year old *Heucherella* 'Tapestry' in bloom growing in the garden in early summer in Canby, Oreg.

FIG. 3 shows the same plant the next winter.

DETAILED PLANT DESCRIPTION

The following is a detailed description of the new *Heucherella* cultivar based on observations of a one-year-old specimen growing in a 1 gallon container in a cool greenhouse in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:

*Form.*—Basal rosette, herbaceous perennial.
*Hardiness.*—USDA Zone 4 to 9.
*Size.*—14 cm tall from top of the foliage to the ground and 25 cm wide.
*Habit.*—Mounding.
*Vigor.*—Excellent.
*Roots.*—Fibrous, freely branching, fine, and white in color; roots develop easily from cuttings.

Leaf:

*Type.*—Simple.
*Arrangement.*—Rosette.
*Shape.*—Ovate to broadly ovate.
*Lobing/division.*—5 main rounded lobes with the terminal the longest, each with rounded secondary lobes.
*Venation.*—Palmate.
*Margins.*—Crenate.
*Apex.*—Mucronulate.
*Base.*—Cordate, overlapping.

*Blade size.*—Usually 9 cm wide and 10 cm long (range from 5 cm to 13 cm long and 5.5 cm to 13 cm wide).

*Surface texture.*—Sparsely glandular both surfaces.

*Texture.*—Thin, leathery.

*Petiole description.*—8 cm to 12 cm long and 2.5 mm wide, glandular hairs, Yellow Green RHS 146B tinted with Brown RHS 200C near the base.

*Leaf color.*—Spring top side — Green RHS 137A with a dark pattern along the veins, between Greyed Purple RHS 187A and Black RHS 202A and a veil or overlay of Greyed Green RHS 190A making the leaf have a blue tone. Spring bottom side — Green RHS 137C with a light brown shade where pattern is on top. Fall and winter topside — Green RHS 138A with the blotch closest to Brown RHS 200A and the veil Grey RHS 201C.

Inflorescence:

*Size.*—Grows to 5 cm wide and 20 cm long.

*Type.*—Thryse.

*Number of flowers per raceme.*—About 150 per thryse.

*Number of raceme.*—11.

*Peduncle.*—48 cm tall, 3 mm wide at base, Brown RHS 200B, glandular hairs, with 0 to 1 petiolate cauline leaves (ovate, blades 1.5 cm to 4.5 cm long and 1.5 cm to 4 cm wide with 3 to 5 lobes, no blotch, margin serrate and Greyed Purple RHS 187A, blade Green RHS 137A).

*Pedicel.*—Variable, with glandular hairs, Brown RHS 100B.

*Bloom period.*—May through June in Canby, Oreg.

Flower bud:

*Size.*—2.5 mm wide and 4 mm long.

*Description.*—Glandular puberulent, ovoid.

*Color.*—Red Purple 74C.

Flower:

*Type.*—Perfect.

*Shape.*—Starry.

*Size.*—4 mm long and 7 mm wide.

*Petal description.*—5 in number, lanceolate; 3.5 mm long, tip acuminate, base attenuate, margin entire, glabrous on top side, sparsely glandular on bottom; Red Purple RHS 73D on both sides.

*Calyx description.*—5 mm long and 5 mm wide, with 5 lobes, divided ½ way to the base, campanulate, glandular inside and out, tip acute, margin entire, lobes inside and outside Red Purple RHS 74C, tube inside Red Purple RHS 73D, tube outside Red Purple RHS 74D.

*Stamen description.*—5, filaments 3 mm long, Red Purple RHS 73D, anthers sterile, less than 1 mm, Grey Brown RHS 199B.

*Pistil description.*—One central two beaked pistil, 6 mm long, Red Purple RHS 73D overall.

*Fragrance.*—None.

*Lastingness.*—Each raceme blooms for about 2 weeks on the plant.

Fruit and seed: None.

Disease and pest tolerance: Although never seen, there is no known resistance to rust, a common problem with *Heucherella.* Excellent disease tolerance to powdery mildew. All *Heucherella* are susceptible to root weevils.

COMPARISON TO SIMILAR *HEUCHERELLA*

Compared to *Heucherella* 'Viking Ship' (U.S. Plant Pat. No. 14,825), this new variety is larger and has colored leaves rather than just green leaves.

Compared to *Heucherella* 'Heart of Darkness' (U.S. Plant Pat. No. 14,489), the new variety has warm pink rather than white flowers and strongly lobed leaves rather than slightly lobed.

The *Heuchera* seed parent, 507, had strongly veiled green leaves with red flowers. The *Tiarella* pollen parent was a well cut and well marked selection.

I claim:

1. A new and distinct *Heucherella* plant as herein illustrated and described.

* * * * *

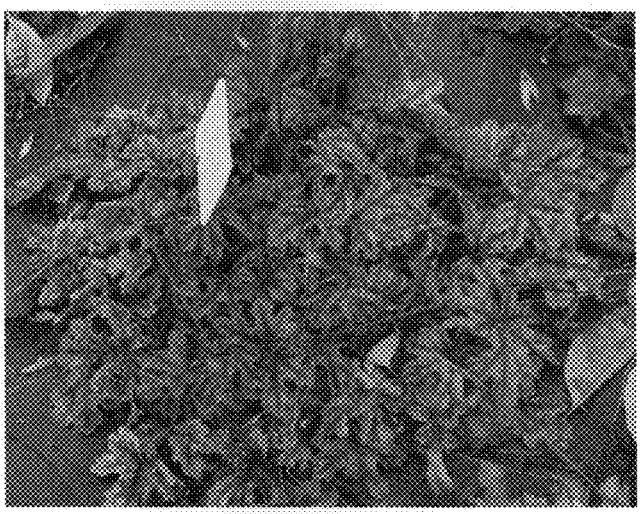

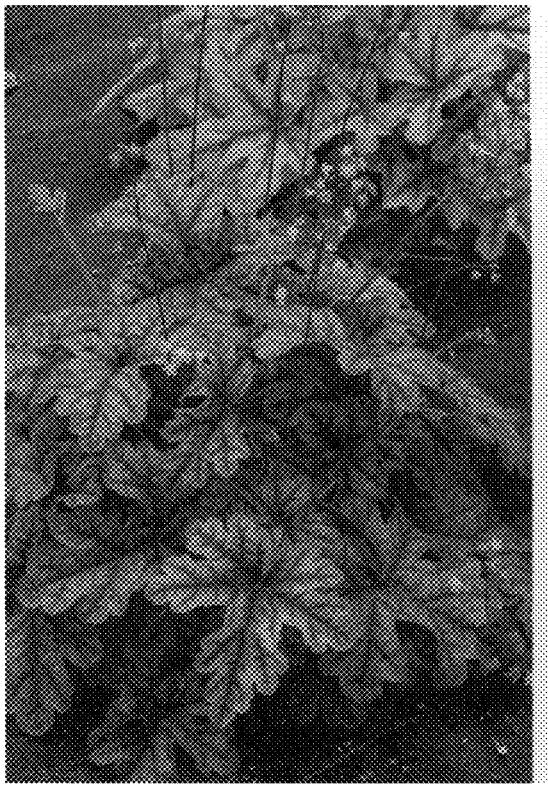
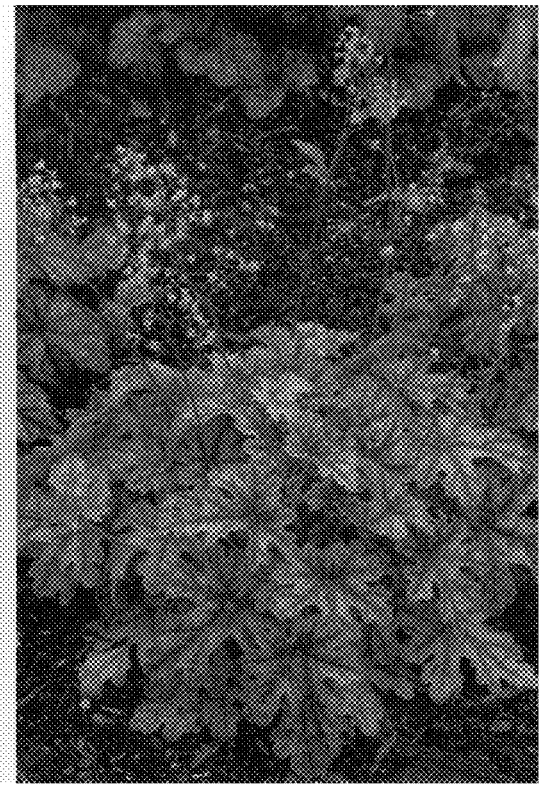
Figure 1 above left, figure 2 above right, figure 3 below